United States Patent [19]

Murakami et al.

[11] 4,202,990
[45] May 13, 1980

[54] PROCESS FOR PRODUCING UNSATURATED CARBOXYLIC ACID ESTERS

[75] Inventors: Fumiki Murakami, Otake; Soichi Teshima, Yamaguchi; Toshihiko Yokoyama, Otake, all of Japan

[73] Assignee: Mitsubishi Rayon Company, Limited, Tokyo, Japan

[21] Appl. No.: 872,876

[22] Filed: Jan. 27, 1978

[30] Foreign Application Priority Data

Feb. 10, 1977 [JP] Japan .................. 52/13588
May 16, 1977 [JP] Japan .................. 52/56115

[51] Int. Cl.² .................. C07C 67/03; C07C 69/54
[52] U.S. Cl. .................. 560/217; 560/222
[58] Field of Search .................. 560/217, 222

[56] References Cited

U.S. PATENT DOCUMENTS 3,642,877  2/1972  Jayawant .................. 560/217

OTHER PUBLICATIONS

Matsukura, Tomita et al., "Polyester Compositiona", Japan 72 26,437, (See Chemical Abstracts vol. 78 (1973) #59245x).
Chimura, Kazuchika et al., "Polyesters", Japan 73 32,194 (See Chemical Abstracts vol. 81 (1974) #26,206u).
Kaeriyama, Kyoji et al., "Effects of Carbon Tetrachloride on Polymerization by Metal Complexes of Beta--Diketones," (See Chemical Abstracts vol. 75 (1971) #152,193b).
Hirooka, Masaaki et al., "Alternating Copolymers", Ger. Offen. 1,949,370, (See Chemical Abstracts vol. 73 (1970) #15,492t).

*Primary Examiner*—Bernard Helfin
*Assistant Examiner*—L. Hendriksen
*Attorney, Agent, or Firm*—Oblon, Fisher, Spivak, McClelland & Maier

[57] ABSTRACT

An ester of an unsaturated carboxylic acid is prepared by an ester exchange process which comprises reacting a lower alkyl ester of an unsaturated, 3-4 carbon atom carboxylic acid with a higher alcohol than the alcohol fragment of said lower alkyl ester over a catalyst selected from the group consisting of (1) chelate compounds of zirconium with $\beta$-diketone or mixtures thereof, (2) chelate compounds of calcium with $\beta$-diketone or mixtures thereof, and mixtures thereof by an ester exchange reaction.

12 Claims, No Drawings

PROCESS FOR PRODUCING UNSATURATED CARBOXYLIC ACID ESTERS

BACKGROUND OF THE INVENTION

Field of the Invention

Esters of unsaturated carboxylic acids can be produced by well known ester exchange reactions. In this type of reaction catalysts are generally used such as sulfuric acid and paratoluenesulfonic acid and alcoholates such as alkali metal alcoholates, aluminum alcoholates and titanium alcoholates. However, these catalysts have their drawbacks. For instance, when an acid catalyst such as sulfuric acid is used, the reaction rate is slow and the production of undesired polymer by-product increases. Furthermore, when a primary alcohol is used as a starting material, an ether by-product is produced. When a secondary alcohol is used as a starting material, a portion of the alcohol is dehydrated and an olefin is formed as a by-product. Other problems exist in that the ester exchange reaction will not proceed with some kinds of alcohols, and the reaction apparatus frequently corrodes.

On the other hand, when an alkali metal alcoholate such as sodium methylate is used as the catalyst, not only do undesirable secondary reactions simultaneously occur such as the by-production of an additional reaction product, the by-production of an alkali metal salt and an anionic polymerization reaction but also complicated procedures are necessary such as the continuous addition of catalyst to the reaction mixture as it loses its activity with the passage of time and the thorough prior dehydration of the catalyst because the catalyst loses its activity with time by reacting with water in the reaction system. Further, the catalyst must be washed with water and removed from the reaction mixture to prevent polymerization before the obtained product is separated from the reaction medium such as by distillation. This is a complicated process step. In addition the process necessitates the treatment of waste water from the reaction.

When aluminum alcoholate or titanium alcoholate is used as the catalyst, not only do the same drawbacks exist as when alkali metal alcoholates are used, but the catalysts lose activity with the passage of time and by the influence of water, but also the catalytic activity of these catalysts will diminish to a level less than the alkali metal alcoholate catalysts. Consequently, the amount of catalyst must be increased or the reaction time must be lengthened. Because of these problems with the conventional catalysts, a need continues to exist for an improved catalyst for ester exchange reactions which overcomes the deficiencies of the conventional catalysts.

SUMMARY OF THE INVENTION

Accordingly, one object of the invention is to provide a catalyst for the ester exchange reaction of carboxylic acid esters of improved activity.

Another object of the invention is to provide a method for conducting the ester exchange reaction of carboxylic acid esters over a catalyst of improved activity.

Briefly, these objects and other objects of the invention as will hereinafter become more readily apparent can be attained by a method for preparing an ester of an unsaturated carboxylic acid by an ester exchange process which comprises reacting a lower alkyl ester of an unsaturated, 3-4 carbon atom carboxylic acid with a higher alcohol than the alcohol fragment of said lower alkyl ester over a catalyst selected from the group consisting of (1) chelate compounds of zirconium with β-diketone or mixtures thereof, (2) chelate compounds of calcium with β-diketone or mixtures thereof, and mixtures thereof by an ester exchange reaction.

DETAILED DESCRIPTION OF THE PREFERRED EMBODIMENTS

Suitable unsaturated carboxylic acid esters which can be used as starting materials in the present invention, include alkyl esters of such monocarboxylic acids as acrylic acid, methacrylic acid and crotonic acid, and alkyl esters of such dicarboxylic acids as fumaric acid and maleic acid. However, the alkyl radical of the ester is a lower alkyl radical than the alkyl radical in the starting material alcohol, and preferably a methyl or ethyl carboxylic acid ester is used. The higher alcohols which are used as a reactant in the present invention include all alcohols having boiling points higher than that of the alcohol produced by the ester exchange reaction. Suitable alcohols can be represented by the following formulae (I) and (II)

$$R\text{-OH} \qquad (I)$$

wherein R stands alkyl or cycloalkyl group having 3 to 20 carbon atoms, $R_1$ and $R_2$ stand alkyl group having 1 to 12 carbon atoms and n stands Number of 2 to 6. Further suitable alcohols include alkoxy alkanols, alkenoxyalkanols, alkenols, alkynols, glycols, triols, polyhydric alcohols higher than triols, phenoxyalkanols, alkylphenoxyalkanols, phenylalkanols, alkylphenylalkanols, alkylmorpholinoalkanols, alkylpiperidinoalkanols, pyridylalkanols, alkanol halides, cyanoalkanols and alkylthioalkanols. Particularly useful and preferable are alcohols containing not less than four carbon atoms. More specific examples of suitable alcohols include n-, i- and t-butanols, 2-ethylhexanol, laurylalcohol, stearylalcohol, cyclohexylalcohol, dimethylaminoethanol, diethylaminoethanol, glycidylalcohol, tetrahydrofurfurylalcohol, ethyleneglycol, triethyleneglycol, tetraethyleneglycol, 1,3-butanediol, allylalcohol and trimethylolpropane. These alcohols can be used as they are without being dehydrated.

The catalyst of the present invention is composed of chelate compounds of zirconium and/or calcium with β-diketone. Suitable chelate compounds include the acetylacetonate, 2.4-hexanedionate, 3.5-heptanedionate, 3-phenylacetylacetonate, 4.4.4-trifluoro-1-phenyl-1.3-butanedionate, 2.2.6.6-tetramethyl-3.5-heptanedionate, 1.1.1-trifluoro-5.5-dimethyl-2.4-hexanedionate and 1.1.1-trifluoro-2.4-pentanedionate of zirconium and calcium.

Among these catalysts, from the viewpoint of catalytic activity and cost, zirconium acetylacetonate and calcium acetylacetonate are particularly preferred.

These above enumerated catalysts can be used singly or in mixtures.

In the present reaction, a solvent is normally used which forms an azeotropic mixture with the alcohol produced in the ester exchange reaction and which is inert to the reaction. Suitable solvents include hexane, benzene and cyclohexane.

Because polymerizable substances are handled in the present reaction, it is preferred to conduct the reaction in the presence of a polymerization inhibitor. Suitable polymerization inhibitors include hydroquinone, hydroquinone monomethyl ether, di-t-butylcatechol, phenothiazine, p-phenylenediamine and methylene blue.

In the present invention, the mole ratio of the alkyl ester of the unsaturated carboxylic acid to the alcohol is 1.0 to 10:1, preferably 1.1 to 5.0:1. Needless to say, any other ratio may be used, but there is no advantage in doing so from the viewpoint of economy.

All of the catalyst may be used from the first, or the catalyst may be added in increments over regular intervals or it may be continuously added to the reaction mixture. However, during normal operations, all of the catalyst is preferably present from the start of the reaction.

The amount of catalyst used can vary considerably. However, it is generally used in amounts of 0.0001 to 1.0 mole per mole of the starting material alcohol, preferably 0.0002 to 0.5 mole in case of zirconium catalyst and 0.0002 to 0.05 mole in case of calcium catalyst.

The temperature usually employed for the ester exchange reaction ranges from 30° to 150° C., preferably 60° to 140° C. The reaction can also be conducted under a reduced pressure.

Having generally described the invention, a more complete understanding can be obtained by reference to certain specific examples, which are provided herein for purposes of illustration only and are not intended to be limiting unless otherwise specified.

In the examples and control examples, the unreacted starting materials and reaction products were quantitatively determined by gas chromatography. The conversion rate of the starting alcohol and the yield of the product ester were represented on the basis of the starting alcohol (ROH). That is to say, yield and conversion were calculated by formulas (1) and (2):

$$\text{(ROH) Conversion} = \frac{\text{Charge ROH (moles)} - \text{Unreacted ROH (moles)}}{\text{Charge ROH (moles)}} \times 100 \quad (1)$$

$$\text{Yield of Product Ester} = \frac{\text{Produced ester (moles)}}{\text{Charge ROH (moles)}} \times 100 \quad (2)$$

EXAMPLE 1

An 74.1 g (1.0 mole) amount of n-butanol, 250.2 g (2.5 moles) of methyl methacrylate, 0.488 g (0.001 mole) of zirconium acetylacetonate and 0.28 g of hydroquinone monomethyl ether were added to a one liter flask fitted with an agitator, thermometer and fractionating tower and were heated and agitated. An azeotropic mixture of methyl methacrylate and methanol from the upper part (top) of the fractionating tower was removed at a reflux ratio of 5 to 10:1 to continuously advance the reaction. The reaction was conducted for 1.5 hours while the temperature at the top was 65° to 70° C. and the flask temperature was 104° to 130° C. The reaction showed a 99.5% conversion of n-butanol and a 99.2% yield of n-butyl methacrylate.

When this reaction solution was directly distilled, 140 g of a fraction of 93° to 94° C. under 80 mmHg were obtained. This fraction was found by gas chromatography to be n-butyl methacrylate at a yield of 98.5%. It is clear that this reaction mixture can be distilled directly without the necessity of any intermediate process step such as water-washing.

EXAMPLE 2

The reaction was performed for two hours by adding 172.2 g (2.0 moles) of methyl acrylate in the apparatus of Example 1 instead of the methyl methacrylate. The results of the experiment were 98.4% conversion of n-butanol and 97.6% yield of n-butyl acrylate. When this ester was distilled in the same manner as in Example 1, it was recovered in a 96.6% yield.

EXAMPLE 3-5

The reactions were performed by adding 1.0 mole of various alcohols which are shown in Table 1 and 2.0 moles of methyl methacrylate in the apparatus of Example 1 instead of the n-butanol and of the 2.5 moles of methyl methacrylate.

The reaction results are shown in Table 1.

Table 1

| Example No. | alcohol | reaction time (hr) | alcohol conversion (%) | ester yield (%) |
|---|---|---|---|---|
| 3 | iso-butanol | 2.0 | 98.8 | 98.4 |
| 4 | 2-ethyl hexanol | 2.0 | 99.1 | 98.5 |
| 5 | Lauryl alcohol | 2.0 | 98.5 | 98.0 |

EXAMPLE 6

89.1 g (1.0 mole) of dimethyl aminoethanol, 250.2 g (2.5 moles) of methyl methacrylate, 0.4 g of phenothiazine and 2.44 g (0.005 mole) of zirconium acetylacetonate were added to the apparatus of Example 1. The reaction was conducted in the same manner as in Example 1 for three hours except an azeotropic mixture of methyl methacrylate and methanol was removed at a reflux ratio of 2 to 10:1. While the reaction was proceeding, the temperature at the top pf the tower was 65° to 75° C. and the flask temperature was 104° to 127° C. The reaction showed a 99.9% conversion of dimethyl aminoethanol and a 99.3% yield of dimethyl aminomethacrylate.

When this reaction solution was directly distilled 155 g of a fraction of 67°-68° C. under 10 mmHg were obtained. This fraction was found by gas chromatography to be dimethyl aminomethacrylate at a yield of 98.7%. It is clear that this reaction mixture can be distilled directly without the necessity of any intermediate process step such as water-washing.

EXAMPLE 7

The reaction was performed for three hours by adding 0.24 g (0.001 mole) of calcium acetylacetonate in the apparatus of Example 1 instead of the zirconium acetylacetonate. An azeotropic mixture of methyl methacrylate and methanol was removed at a reflux ratio of 2 to 10:1. The reaction showed a 99.5% conversion of n-butanol and a 99.0% yield of n-butyl methacrylate. When this reaction solution was directly distilled, 139 g of a fraction of 93°-94° C. under 80 mmHg were obtained. This fraction was found by gas chromatography to be n-butyl methacrylate at a yield of 97.8%.

EXAMPLE 8

The reaction was performed for 3 hours in the same manner as in Example 2 except adding 0.48 g (0.002 mole) of calcium acetylacetonate and 0.2 g of hydroquinone monomethyl ether instead of zirconium acetyl acetonate and 0.28 g of hydroquinone monomethyl ether. The results were a 99.1% conversion of n-butanol and 98.5% yield of n-butylacrylate. This ester was recovered in a 97.5% yield by direct distillation.

EXAMPLE 9–15

In to the apparatus described in Example 1 were placed 1.0 mole of an alcohol shown in Table 2, 2.0 moles of methyl methacrylate per hydroxyl radical of the alcohol, calcium acetyl acetonate which amount are shown in Table 2 and 0.3 g of hydroquinone monomethyl ether. The reactions were carried out in the same manner as in Example 7.

The reaction results are shown in Table 2.

TABLE 2

| Example No. | Alcohol | mole ratio of the catalyst to an alcohol | Reaction time (hr) | Alcohol conversion (%) | Ester yield (%) |
|---|---|---|---|---|---|
| 9 | iso-butanol | 0.001 | 3.6 | 99.0 | 98.5 |
| 10 | 2-ethylhexanol | 0.001 | 2.5 | 99.3 | 98.7 |
| 11 | Lauryl alcohol | 0.001 | 2.5 | 99.1 | 98.4 |
| 12 | Dimethyl aminoethanol | 0.01 | 6.0 | 98.2 | 97.0 |
| 13 | Diethyl aminoethanol | 0.01 | 6.0 | 98.0 | 97.2 |
| 14 | Ethyleneglycol | 0.005 | 4.0 | 99.9 | 96.7 |
| 15 | 1.3-butanediol | 0.005 | 4.0 | 99.9 | 96.3 |

EXAMPLE 16–17

Into the apparatus described in Example 1 were placed 1.0 mole of an alcohol shown in Table 3, 2.0 moles of methyl methacrylate per hydroxyl radical of the alcohol, calcium and zirconium acetylacetonate and 0.3 g of hydroquinone monomethyl ether.

The reactions were conducted in the same manner as in Example 7.

The reaction results are shown in Table 3.

TABLE 3

| Example No. | Alcohol | mole ratio of the catalyst to an alcohol | Reaction time (hr) | Alcohol conversion (%) | Ester yield (%) |
|---|---|---|---|---|---|
| 16 | Ethylene glycol | Ca : 0.003 Zr : 0.005 | 4.0 | 99.9 | 95.8 |
| 17 | Dimethyl aminoethanol | Ca : 0.005 Zr : 0.003 | 4.0 | 99.9 | 99.0 |

All reactions described in Example 1 to 17 were carried out without a dehydrating operation in advance. Though a starting material contains 0.005 to 0.007 mole of water per 1 mole of an alcohol, there is no influence to advance the reaction and showed the excellent results. Therefore it is clear that the dehydrating operation before starting the reaction can be omitted and the secondary reactions such as hydrolysis are few and very little acrylic and methacrylic acid is produced as a by-product. Further, the treatment of the catalyst after the reaction is easy. These are substantial industrial advantages.

CONTROL EXPERIMENT 1

74.1 g (1.0 mole) of n-butanol, 250.2 g (2.5 moles) of methyl methacrylate, 0.25 g of hydroquinonemonomethyl ether and 2.45 (0.025 mole) of concentrated sulfuric acid were added to a flask to conduct a reaction in the same manner as in Example 1. The reaction was carried out for 6 hours. The reaction results were 96.5% conversion of n-butanol and 91.2% yield of n-butyl methacrylate. However, it was found by gas chromatography that a high boiling point by-product was present and 0.004 mole of methacrylic acid (2660 ppm. based on n-butyl methacrylate) was produced as a by product.

When this reaction solution was directly distilled in the same manner described in Example 1, the methyl methacrylate fraction polymerized when the distillation was finished and butyl methacrylate could not be recovered. Further, after the reaction was finished, when the reaction solution was washed twice with 10% caustic soda solution and was then distilled in the same manner described in Example 1, 122 g of a butyl methacrylate fraction were obtained. Therefore, the yield of ester was only 85.8%.

CONTROL EXPERIMENT 2

A 74.1 g (1.0 mole) amount of n-butyl alcohol, 250.2 g (2.5 mols) of methyl methacrylate, 187 g (2.18 mols) of n-hexane and 0.17 g of hydroquinonemonomethyl ether were added to the apparatus described in Example 1 and were heated and agitated under full reflux to remove water from the reaction system. The amount of water obtained in the reaction solution was 0.001 mol. To the reaction solution was added 0.0035 mol of sodium methylate as a catalyst and the solution was heated and agitated. An azeotropic mixture of n-hexane and methanol from the upper part (top) of the fractionating tower was obtained and was kept stationary in a decanter. The n-hexane layer which separated was returned to the tower and the methanol layer was removed continuously to advance the reaction. Meanwhile, the temperature at the top of the tower was 56° to 59.8° C. and the flask temperature was 83° to 90° C. The results of the experiment were a 99.4% conversion of n-butyl alcohol and a 87.3% yield of n-butyl methacrylate. However, it was found by gas chromatography that an additive of methyl methacrylate was produced as a by-product as well as a polymer. As soon as this reaction solution was distilled, it polymerized.

It was also found that if the reaction was conducted without a dehydrating operation, it soon stopped. Even when the reaction was conducted for 5 hours, the conversion of n-butyl alcohol was only 32.1% and the yield of n-butyl methacrylate was only 25.9%.

CONTROL EXPERIMENT 3

89.1 g (1.0 mole) amount of dimethylaminoethanol, 250.2 g (2.5 moles) of methyl methacrylate, 187 g (2.18 moles) of n-hexane and 0.17 g of hydroquinonemonomethyl ether were added to the apparatus described in Example 1, and were heated and agitated under full reflux to remove water from the reaction system. The concentration of water obtained in the reaction solution was 60 ppm. This amount corresponds 0.0018 mole ratio of water to starting material alcohol.

To the reaction solution was added 0.0035 mole of sodium methylate as a catalyst, and the reaction was initiated. An azeotropic mixture of n-hexane and methanol from the upper part (top) of the fractionating tower was obtained and was kept stationary in a decanter. The n-hexane layer was returned to the tower and the methanol layer was removed continuously to advance the reaction. Meanwhile, the temperature at the top of the tower was 55°–59° C. and the flask temperature was 84°–90° C. The reaction was carried out for 3 hours. The results were a 99.0% conversion of dimethylaminoethylalcohol and a 83.4% yield of dimethylaminoethyl methacrylate. However, it was found by gas chromatography that an additive to double bond of methyl methacrylate was produced as a by product as well as a polymer. As soon as this reaction solution was distilled, it polymerized.

It was also found that if the reaction was conducted without a dehydrating operation, it soon stopped. Even when the reaction was carried out for 5 hours, the conversion of dimethylaminoethanol was 35.3% and the yield of dimethylaminoethyl methacrylate was only 28.5%.

CONTROL EXPERIMENT 4

62.07 g (1.0 mole) of ethyleneglycol, 450.5 g (4.5 moles) of methyl methacrylate, 129.3 g (1.5 moles) of n-hexane and 1.0 g of hydroquinone monomethyl ether were added to the apparatus described in Example 1, and were heated and agitated for one hour under full reflux to remove water from reaction system. The amount of water obtained in the reaction solution was 0.001 mole.

To the solution was added 0.0035 mole of sodium methylate as a catalyst and heated and agitated. An azeotropic mixture of n-hexane and methanol from the upper part of the fractionating tower was obtained and was kept stationary in a decanter. The n-hexane layer was returned to the tower and the methanol layer was removed continuously to advance the reaction. Meanwhile, the temperature at the top of the tower was 56°–59° C. and the flask temperature was 80°–90° C. The reaction was carried out for three hours. The results were a 99.9% conversion of ethyleneglycol and a 85.7% yield of ethylenedimethacrylate. However it was found by gas chromatography that an additive to double bond of methyl methacrylate was produced as a by product. As soon as this reaction solution was distilled, it polymerized.

It was also found that if the reaction was conducted without a dehydrating operation, it soon stopped. Even when the reaction was carried out for 8 hours, the conversion of ethyleneglycol was 51.4% and the yield of ethylenedimethacrylate was only 6.2%.

Having now fully described this invention, it will be apparent to one of ordinary skill in the art that many changes and modifications can be made thereto without departing from the spirit or scope of the invention as set forth herein.

We claim:

1. An ester exchange process, which comprises: preparing an ester of an unsaturated carboxylic acid by reacting a lower alkyl ester of an $\alpha,\beta$-unsaturated, 3–4 carbon atom carboxylic acid with an alcohol higher than the alcohol fragment of said lower alkyl ester over a catalyst selected from the group consisting of (1) chelate compounds of zirconium with at least one $\beta$-diketone compound, (2) chelate compounds of calcium with at least one $\beta$-diketone compound and (3) mixtures of said calcium and zirconium chelates by an ester exchange reaction.

2. The process of claim 1, wherein said lower alkyl ester is a methyl or ethyl ester and said higher alcohol is one having boiling point higher than that of the alcohol produced by the exchange reaction.

3. The process of claim 2, wherein the higher alcohol is a compound of formula (I) or (II)

$$ROH \quad\quad (I)$$

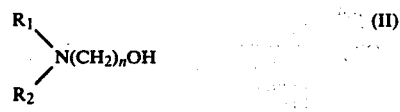

(II)

wherein R represents alkyl or cycloalkyl having 3 to 20 carbon atoms, $R_1$ and $R_2$ represent alkyl of 1 to 12 carbon atoms and n represents a number from 2 to 6.

4. The process of claim 1, wherein the mole ratio of the catalyst relative to said higher alcohol ranges from 0.0001 to 1.0:1.

5. The process of claim 1, wherein said catalyst is zirconium acetyl acetonate.

6. The process of claim 5, wherein the mole ratio of the catalyst relative to said higher alcohol ranges from 0.0002 to 0.5:1.

7. The process of claim 1, wherein said catalyst is a chelate compound of calcium with a $\beta$-diketone.

8. The process of claim 7, wherein the mole ratio of the catalyst relative to said higher alcohol ranges from 0.0002 to 0.05:1.

9. The process of claim 7, wherein said catalyst is calcium acetylacetonate.

10. The process of claim 1, wherein the reaction temperature is 30° to 150° C.

11. The process of claim 1, wherein said $\beta$-diketone compound is acetylacetone, 2,4-hexandione, 3,5-heptanedione, 3-phenylacetylacetone, 4,4,4-trifluoro-1-phenyl-1,3-butanedione, 2,2,6,6-tetramethyl-3,5-heptanedione, 1,1,1-trifluoro-5,5-dimethyl-2,4-hexanedione or 1,1,1-trifluoro-2,4-pentanedione.

12. The process of claim 1, wherein said ester exchange reaction is conducted in the presence of a polymerization inhibitor.

* * * * *